United States Patent
Smith (10) Patent No.: US 9,386,980 B2
(45) Date of Patent: Jul. 12, 2016

(54) WOUND CLOSURE DEVICE INCLUDING DIRECT-DRIVEN NEEDLE

(71) Applicant: COVIDIEN LP, Mansfield, MA (US)

(72) Inventor: Robert C. Smith, Middlefield, CT (US)

(73) Assignee: COVIDIEN LP, Mansfield, MA (US)

(*) Notice: Subject to any disclaimer, the term of this patent is extended or adjusted under 35 U.S.C. 154(b) by 351 days.

(21) Appl. No.: 14/069,108

(22) Filed: Oct. 31, 2013

(65) Prior Publication Data

US 2014/0058415 A1 Feb. 27, 2014

Related U.S. Application Data

(62) Division of application No. 12/887,902, filed on Sep. 22, 2010, now Pat. No. 8,591,529.

(60) Provisional application No. 61/247,644, filed on Oct. 1, 2009.

(51) Int. Cl.
| | |
|---|---|
| *A61B 17/04* | (2006.01) |
| *A61B 17/062* | (2006.01) |
| *A61B 17/29* | (2006.01) |
| *A61B 17/06* | (2006.01) |

(52) U.S. Cl.
CPC ......... *A61B 17/0469* (2013.01); *A61B 17/0482* (2013.01); *A61B 17/062* (2013.01); *A61B 17/29* (2013.01); *A61B 2017/06042* (2013.01); *A61B 2017/2926* (2013.01)

(58) Field of Classification Search
CPC ........... A61B 17/0469; A61B 17/0482; A61B 17/062; A61B 2017/06042; A61B 17/29; A61B 2017/2926
See application file for complete search history.

(56) References Cited

U.S. PATENT DOCUMENTS

| | | |
|---|---|---|
| 5,470,338 A | 11/1995 | Whitfield et al. |
| 7,211,093 B2 | 5/2007 | Sauer et al. |
| 7,235,087 B2 | 6/2007 | Modesitt et al. |
| 7,449,024 B2 | 11/2008 | Stafford |
| 2004/0044365 A1 | 3/2004 | Bachman |
| 2005/0149065 A1 | 7/2005 | Modesitt |

(Continued)

FOREIGN PATENT DOCUMENTS

| | | |
|---|---|---|
| EP | 1354558 A2 | 10/2003 |
| EP | 1629780 A1 | 3/2006 |

(Continued)

OTHER PUBLICATIONS

European Office Action issued in corresponding EP application No. 10251696 on Dec. 7, 2015.

*Primary Examiner* — Gregory Anderson
*Assistant Examiner* — Son Dang (57) ABSTRACT

A suturing device includes a housing, a rod, a ferrule assembly, and a needle. The housing defines a guide lumen extending longitudinally therethrough. The rod is engaged with the housing and extends distally therefrom. The ferrule assembly is disposed at a distal end of the rod and is configured to releasably retain a ferrule therein. The ferrule is adapted to retain a portion of a suture therein. The needle is configured for translation through the guide lumen defined within the housing. A distal end of the needle is configured to engage the ferrule within the ferrule assembly for removal of the ferrule from the ferrule assembly.

7 Claims, 6 Drawing Sheets

(56) References Cited

U.S. PATENT DOCUMENTS

| | | |
|---|---|---|
| 2005/0154402 A1 | 7/2005 | Sauer et al. |
| 2005/0154403 A1 | 7/2005 | Sauer et al. |
| 2006/0030868 A1 | 2/2006 | Bennett |
| 2006/0069397 A1 | 3/2006 | Nobles et al. |
| 2007/0032799 A1* | 2/2007 | Pantages ............ A61B 17/0057 606/144 |
| 2008/0045979 A1 | 2/2008 | Ma |
| 2009/0105729 A1 | 4/2009 | Zentgraf |

FOREIGN PATENT DOCUMENTS

| | | |
|---|---|---|
| WO | 02/24078 A1 | 3/2002 |
| WO | 2010085793 A2 | 7/2010 |
| WO | 2010105046 A1 | 9/2010 |

* cited by examiner

WOUND CLOSURE DEVICE INCLUDING DIRECT-DRIVEN NEEDLE

CROSS-REFERENCE TO RELATED APPLICATION

The present application is a divisional application of U.S. patent application Ser. No. 12/887,902, filed on Sep. 22, 2010, which claims the benefit of and priority to U.S. Provisional Application Ser. No. 61/247,644 filed on Oct. 1, 2009, the entire contents of each of which are incorporated herein by reference.

BACKGROUND

1. Technical Field

The present disclosure relates to a wound closure device and, more particularly, to a wound closure device having a direct driven needle for suturing a wound.

2. Description of Related Art

Puncture wounds, wounds that pierce through tissue, may result from trauma or may be intentionally created in order to provide access to a body cavity during surgical procedures. During endoscopic surgical procedures, for example, a trocar device is utilized to puncture the peritoneum to provide an access port by way of a cannula through the abdominal wall. Generally, a trocar and/or cannula is placed through the abdominal wall for introduction of surgical instrumentation which is necessary to carry out the surgical procedure. In this manner, the surgeon may introduce a surgical instrument such as a grasper, scissor, clip applier, stapler or any other surgical instrument which may be necessary during the particular surgical procedure. Once the procedure is complete, it is necessary to suture the wound.

Conventional instruments for closing puncture wounds generally include a shaft that can be extended into the body through either the puncture wound itself (in the case of a puncture caused by trauma) or through a cannula (in the case of a puncture created to access a surgical site). Suture retaining needles are then deployed from the shaft into tissue. Unfortunately, the mechanisms used for deploying the needles are often cumbersome and may make the extension and/or retraction of the suturing device difficult.

In the prior art, U.S. Pat. No. 5,470,338 discloses a suturing instrument for closing trocar puncture wounds. The suturing instrument includes a pair of needle carriers having needles releasably retained thereon. The needle carriers are translatable from a retracted position to a deployed position via a rack and pinion mechanism to urge the needles into tissue. U.S. Pat. No. 7,235,087 discloses an articulating suturing device including a shaft having an articulated foot disposed at a distal end thereof. The foot includes suture attachment cuffs that lockingly engage needles such that the cuffs can be withdrawn upon withdrawal of the needles. U.S. Pat. No. 7,449,024 discloses a suturing device having at least two arms that are extendable from the shaft of the suturing device. The arms are rotated about a pivot to extend from the shaft. Needles may then be inserted into engagement with the arms to retrieve a suture from the arms. U.S. Patent Application Publication No. 2006/0030868 discloses a suturing device including a pair of wings that are selectively extendable from the device. Needles carrying sutures thereon may then be advanced through tissue and into engagement with the wings to retain the sutures thereon. U.S. Patent Application Publication No. 2006/0069397 discloses a suturing apparatus similar to that of U.S. Pat. No. 7,449,024, discussed above, and further discloses a handle assembly for actuating the suturing apparatus. U.S. Patent Application Publication No. 2008/0045979 discloses an articulating suturing device similar to that of U.S. Pat. No. 7,235,087, discussed above.

SUMMARY

In accordance with one embodiment of the present disclosure, a suturing device is provided. The suturing device includes a housing defining a guide lumen extending longitudinally therethrough. A rod is engaged with the housing and extends distally therefrom. A ferrule assembly is disposed at a distal end of the rod. The ferrule assembly is configured to releasable retain a ferrule therein. The ferrule is adapted to retain of a portion of a suture therein. A needle is configured for translation through the guide lumen defined within the housing. A distal end of the needle is configured to engage the ferrule within the ferrule assembly for removal of the ferrule from the ferrule assembly.

In one embodiment, the ferrule assembly includes a curved portion and a ferrule holder. One end of the curved portion is attached to the distal end of the rod. The other end of the curved portion retains the ferrule holder thereon. The ferrule is disposed within a lumen defined through the ferrule holder.

In another embodiment, the ferrule assembly and/or the housing includes a tissue stop positionable about a face of tissue upon insertion of the suturing device into a wound in tissue. The tissue stop of the ferrule assembly may be configured to engage the rod and to releasable retain the ferrule therein.

In yet another embodiment, the needle and the ferrule are configured to engage each other in a male-female friction fit engagement.

In still another embodiment, the rod is selectively securable within the housing along a length of the rod. The rod is securable within the housing between a first position in which the rod extends a minimum distance distally from the housing and a second position in which the rod extends a maximum distance distally from the housing.

In still yet another embodiment, the ferrule assembly includes one or more compliance features configured to reduce the likelihood of damaging the suturing instrument and/or surrounding tissue.

A method of suturing a wound is also provided in accordance with the present disclosure. The method includes providing a suturing device according to any of the above embodiments. The method further includes inserting the suturing device through a wound such that the ferrule assembly is disposed on an interior surface of tissue to be sutured, inserting the needle into the guide lumen and through tissue to engage the ferrule, translating the needle proximally to remove the ferrule from the ferrule assembly, and translating the needle proximally back through tissue, thereby passing the ferrule and the portion of suture attached thereto through tissue.

In one embodiment, the method further includes removing the suturing device from the wound. The suturing device may then be re-loaded and the above-described method may be repeated on an opposite side of the wound. Finally, the sutures disposed through tissue on opposite sides of the wound may be tied off to close the wound.

In yet another embodiment, prior to inserting the suturing device through a wound, the positioning of the rod with respect to the housing may be adjusted according to a thickness of tissue to be sutured.

BRIEF DESCRIPTION OF THE DRAWINGS

Various embodiments of the subject suturing device are described herein with reference to the drawings wherein.

DETAILED DESCRIPTION

In the figures and in the description that follows, in which like reference numerals identify similar or identical elements, the term "proximal" will refer to the end of the apparatus which is closest to the operator during use, while the term "distal" will refer to the end which is farthest from the operator, as is traditional.

Figure 1:
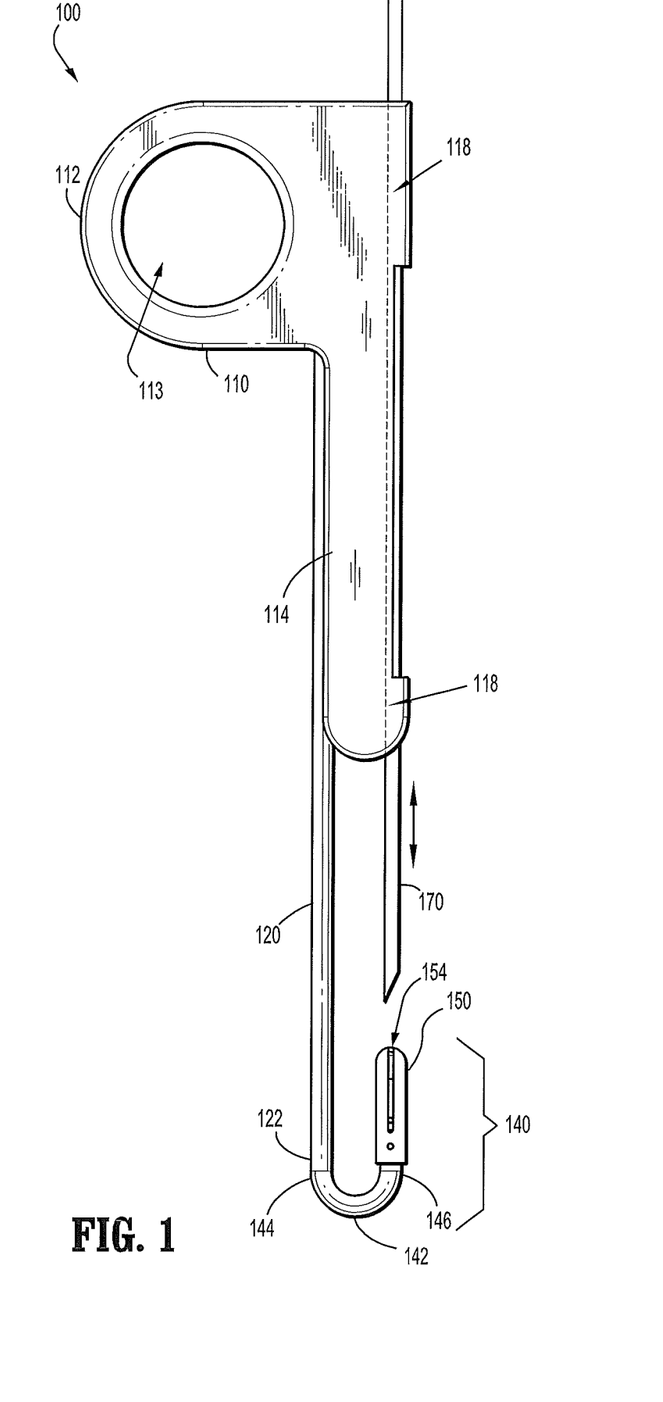
FIG. 1 is a side view of a suturing device according to one embodiment of the present disclosure.
Figures 2, 3:
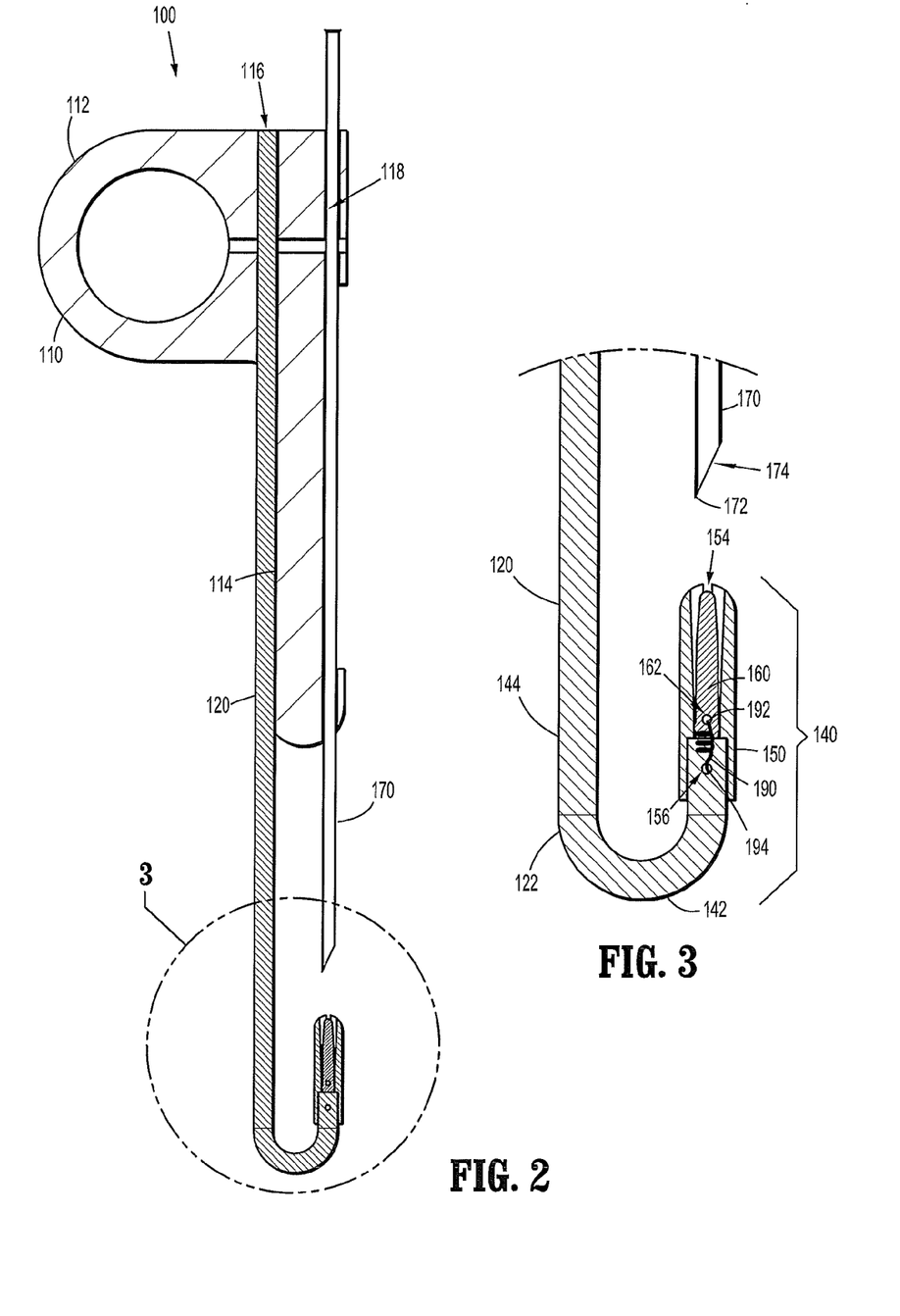
FIG. 2 is a side, cross-sectional view of the suturing device of FIG. 1.
FIG. 3 is an enlarged, cross-sectional view of a ferrule assembly of the suturing device of FIG. 2.

Turning now to FIGS. 1-3, a suturing device 100 is shown generally including a housing 110, a rod 120, a ferrule assembly 140 and a needle 170. Housing 110 includes a proximal portion 112 and an elongated distal portion 114. Proximal portion 112 includes finger ring 113 defined therethrough to allow an operator to grasp the suturing device 100. Rod 120 is disposed through lumen 116 of housing 110 and is fixedly engaged therein, although, as will be described in embodiments below, rod 120 may be selectively translatable with respect to housing 110 to for varying the length of suturing device 100. Rod 120 extends distally from proximal portion 112. A ferrule assembly 140 is disposed at a distal end 122 of rod 120. Ferrule assembly 140 includes a curved, or U-shaped, portion 142, although other configurations, e.g., angled, are contemplated. Curved portion 142 is attached at a first end 144 to the distal end 122 of rod 120. A second end 146 of curved portion 142 is configured to retain ferrule holder 150 thereon. Ferrule holder 150 includes a lumen 154 defined therein. Ferrule 160 is releasable retained within lumen 154 of ferrule holder 150. A portion of a suture 190, e.g., a suture loop 190, is disposed within lumen 154 of ferrule holder 150. Suture loop 190 is disposed through aperture 162 of ferrule 160 at a first end 192 thereof and through aperture 156 of ferrule holder 150 at second end 194 thereof such that suture loop 190 interconnects, or couples ferrule 160 and ferrule holder 150. Alternatively, suture loop 190 may be secured to curved portion 142 of ferrule assembly 140, or may be configured to extend proximally from ferrule holder 150, passing through a lumen (not shown) defined within housing 110.

Referring now to FIGS. 2-3, needle 170, which is disposed through lumen 118 defined within housing 110, includes a distal tip 172 and is configured to translate through lumen 118 to engage ferrule 160. Needle 170 is hollow, defining a lumen 174 therethrough. Once needle 170 is inserted through lumen 118 of housing 110, lumen 118 acts as a guide for needle 170. Specifically, lumen 118 is of sufficiently large diameter to allow needle 170 to readily translate therethrough but is also of sufficiently small diameter as to inhibit needle 170 from angling or tilting within lumen 118. Thus, once needle 170 is inserted into lumen 118 and translated distally therethrough, lumen 118 directs, or guides needle 170 toward ferrule holder 150.

As can be appreciated, upon further distal translation of needle 170 through lumen 118 of housing 110, distal tip 172 of needle 170 eventually enters lumen 154 defined within ferrule holder 150. As mentioned above, lumen 118 guides, or directs needle 170 toward ferrule holder 150, inhibit needle 170 from becoming mis-aligned with ferrule holder 150 as needle 170 is translated through tissue. As needle 170 is urged distally into lumen 154, needle 170 surrounds ferrule 160 1.e., ferrule 160 enters lumen 174 of needle 170. Lumen 174 may have a slightly smaller diameter than ferrule 160 such that, when needle 170 is urged around ferrule 160, ferrule 160 becomes lodged within lumen 174, retaining ferrule 160 therein via a releasable male-female friction-fit engagement. Alternatively, lumen 174 may taper proximally from distal tip 172 from a first diameter which is larger than the diameter of ferrule 160 to a second diameter which is smaller than the diameter of ferrule 160. In this configuration, further urging of ferrule 160 into lumen 174 engages ferrule 160 within lumen 174 in a friction-fit engagement. In another alternative embodiment, needle 170 is of a sufficiently small diameter to engage a lumen (not shown) defined in ferrule 160. In this embodiment, needle 170 may be urged into the lumen defined in ferrule 160 such that the ferrule 160 and needle 170 are engaged in a male-female friction-fit engagement. It is envisioned that any of the above-mentioned configurations of needle 170 and ferrule 160 may be used in accordance with any of the embodiments discussed herein.

As mentioned above, and as shown in FIG. 3, suture 190 is attached to ferrule holder 150 of ferrule assembly 140 (via aperture 156) at one end 194 thereof and to ferrule 160 (via aperture 162) at the other end 192 thereof. In preparation for use, with suture 190 engaged to both ferrule holder 150 and ferrule assembly 140, ferrule 160 is releasably retained within lumen 154 of ferrule holder 150.

With reference again to FIGS. 1-3, the operation of suturing device 100 will be described. Once suture 190 and ferrule 160 are loaded into ferrule holder 150, as described above, suturing device 100 is inserted into a wound to be sutured. Suturing device 100 is translated distally through the wound such that ferrule assembly 140 is positioned adjacent an interior face of tissue and such that elongated distal portion 114 of housing 110 is positioned adjacent an external, or opposing, face of tissue. In other words, suturing device 100 is positioned such that tissue to be sutured is disposed between ferrule assembly 140 and elongated distal portion 114 of housing 110. It is envisioned that a length of rod 120 may be dimensioned according to the thickness or range of thicknesses of tissue to be suture such that the gap between ferrule assembly 140 and elongated distal portion 114 is sufficiently large as to allow tissue having a certain thickness to be disposed therebetween. Thus, for suturing relatively thin tissue, suturing device 100 may be configured such that rod 120 is relatively short in length. On the other hand, if it is desired to suture relatively thick tissue, suturing device 100 may be configured such that rod 120 is relatively long in length. Alternatively, as will be discussed in embodiments discussed below, rod 120 may be adjustable such that suturing device 100 may be used to suture tissues having a wide range of thicknesses.

With tissue to be sutured disposed between the ferrule assembly 140 and the elongated distal portion 114 of housing 110, needle 170 may be inserted through lumen 118 defined within housing 110. In order to maintain suturing device 100 in the position described above, an operator may position a finger through finger ring 113 defined within housing 110. Needle 170 is translated distally through lumen 118 and tissue, guided toward ferrule holder 150 by lumen 118 defined within housing 110. While the operator holds suturing device 100 in position, needle 170 is translated further distally such that distal tip 172 of needle 170 passes completely through tissue to be sutured and enters lumen 154 of ferrule holder 150. Needle 170 is then urged further into engagement with ferrule holder 150 to releasably engage ferrule 160 thereon.

Once needle 170 is inserted into lumen 154 of ferrule holder 150 to engage ferrule 160 within lumen 174 of needle 170, needle 170 may be pulled proximally. As needle 170 is pulled proximally, ferrule 160 is removed from ferrule holder 150. Needle 170 and, thus, ferrule 160 and first end 192 of suture 190, which are engaged thereto, are translated proximally through tissue until needle 170 and ferrule 160 have passed completely through tissue, leaving suture 190 disposed through tissue, e.g., such that first end 192 of suture 190 is disposed on a proximal side of tissue, while second end 194 of suture 190 remains disposed on a distal side of tissue since second end 194 of suture 190 is disposed through aperture 156 of ferrule holder 150. Suturing device 100 may then be removed, reloaded with another ferrule holder 150 having a ferrule 160 disposed thereon, and positioned on an opposite side of the wound. Ferrule 160 may then be removed from lumen 174 of needle 170 such that the above-described method can be repeated on an opposite side of the wound, or at various positions around the wound. Ultimately, the operator may tie off the sutures 190 to suture the wound closed.

Figure 4:
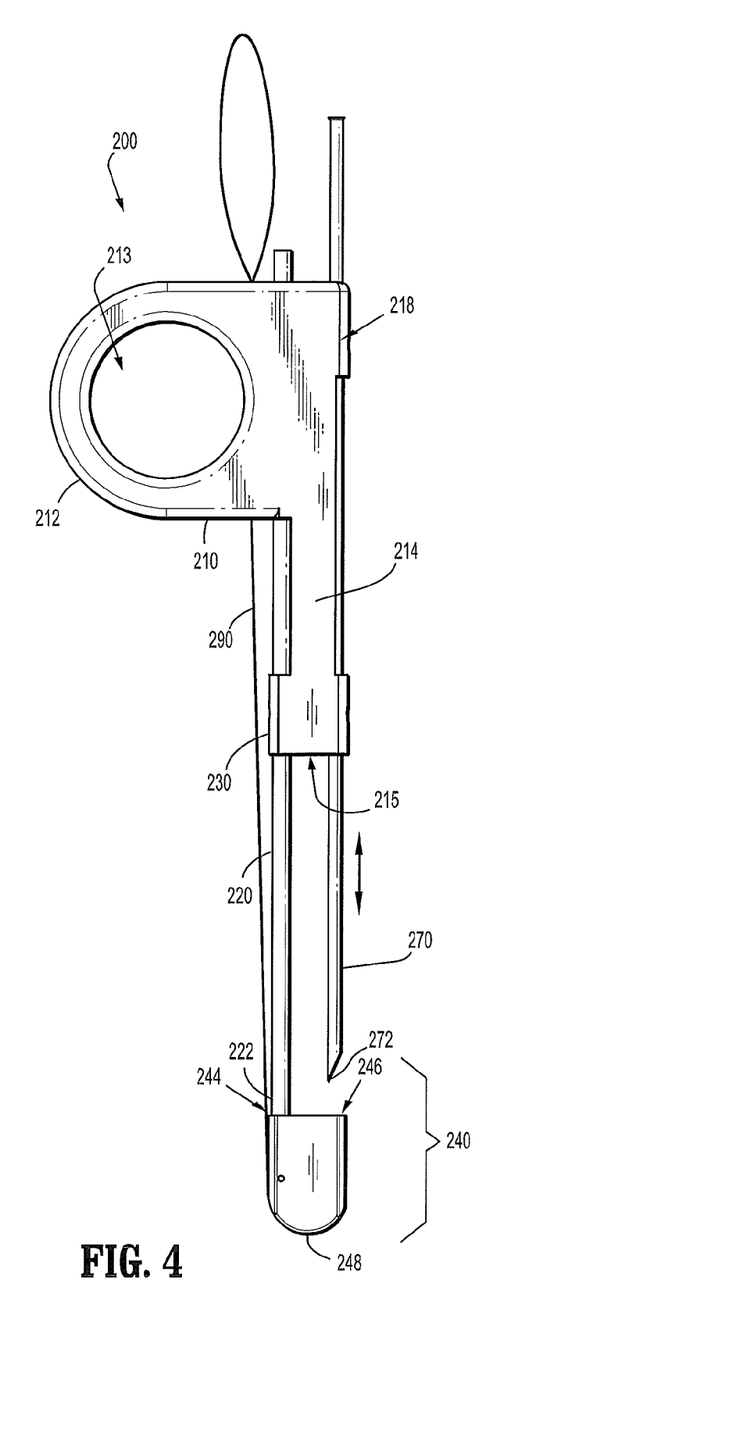
FIG. 4 is a side view of a suturing device according to another embodiment of the present disclosure.
Figure 5:
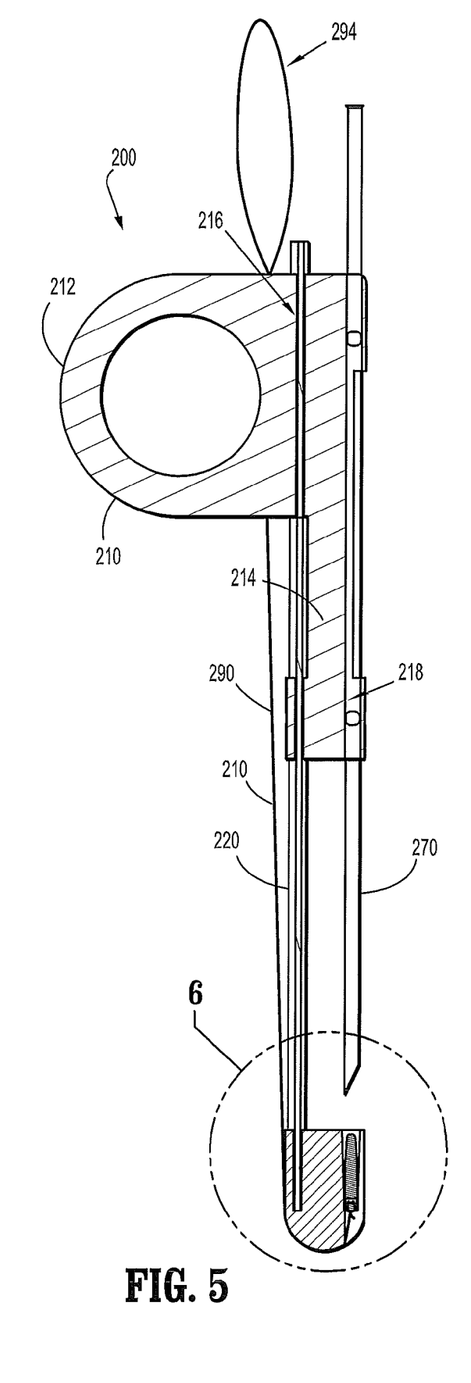
FIG. 5 is a side, cross-sectional view of the suturing device of FIG. 4.
Figure 6:
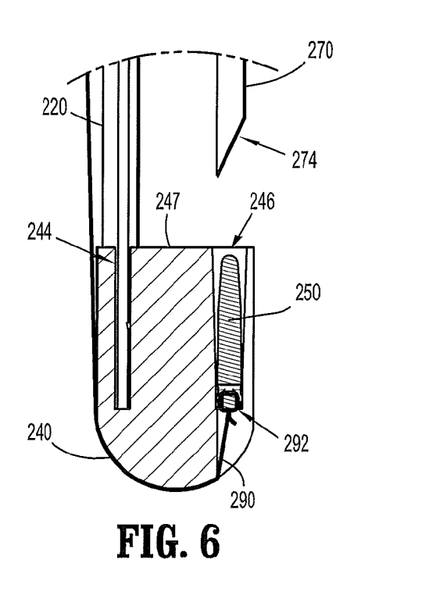
FIG. 6 is an enlarged, cross-sectional view of a ferrule assembly of the suturing device of FIG. 5.

Referring now to FIGS. 4-6, another embodiment of the presently disclosed suturing device 200 is shown. In the embodiment of FIGS. 4-6, as in the previous embodiment, suturing device 200 includes a housing 210, a ferrule assembly 240 and a needle 270. Housing 210 includes a proximal portion 212 and an elongated distal portion 214. Proximal portion 212 includes finger ring 213 defined therethrough. Finger ring 213 is dimensioned to allow an operator to grasp the suturing device 200 with a single hand. Rod 220 is disposed through a lumen 216 defined through housing 210. Rod 220 is selectively positionable within housing 210 via latch 230. More particularly, when latch 230 is disposed in the closed position, as shown in FIG. 4, rod 220 is fixedly secured with respect to housing 210. When latch 230 is released to the open position, rod 220 is translatable through lumen 216 with respect to housing 210. Thus, as can be appreciated, rod 220 may be selectively positioned with respect to housing 210 such that rod 220 extends distally from housing 210 a desired distance. Latch 230 may be any suitable locking mechanism capable of securing rod 220 in position when closed and allowing rod 220 to translate through lumen 116 when open. As mentioned above, the ability to selectively position rod 220 with respect to housing 210 is advantageous in that the suturing device 200 may be used to suture tissues having a wide range of thicknesses. Alternatively, latch 230 may be fixed closed such that, as in the embodiment of FIGS. 4-6, rod 220 is fixed with respect to housing 210.

With continued reference to FIGS. 4-6, ferrule assembly 240 is disposed at a distal end 222 of rod 220. As can be appreciated, depending on the positioning of rod 220 with respect to housing 210, ferrule assembly 240 is either closer to or farther from housing 210. Ferrule assembly 240 includes first and second lumens 244 and 246, respectively, defined in diametrically opposed sides of ferrule assembly 240, although other configurations are contemplated. Lumens 244 and 246 extend from a proximal surface 247 of ferrule assembly 240 partially, but not entirely, therethrough such that distal surface 248 of ferrule assembly 240 defines a continuous surface. Distal surface 248 of ferrule assembly 240 may be generally conically shaped to facilitate the insertion of suturing instrument 200 through an opening in tissue and/or may also include a blunt tip portion to help avoid damaging tissue upon insertion into an opening in tissue. Proximal surface 247 of ferrule assembly 240 may be configured as a tissue stop 247 such that, as will be discussed below, when needle 270 and ferrule 240 are pulled proximally, tissue stop 247 contacts an interior surface of tissue to be sutured, thereby helping to inhibit proximal movement of suturing device 200. Additionally, distal surface 215 of elongated distal portion 214 of housing 210 may also be configured as a tissue stop 215 such that tissue stop 215 helps to inhibit distal translation of suturing device 200 once tissue stop 215 contacts an exterior surface of tissue.

With continued reference to FIGS. 4-6, rod 220 is disposed through first lumen 244 of ferrule assembly 240 and is fixedly secured thereto. Second lumen 246 of ferrule assembly 240 is configured to releasably retain ferrule 250 therein. Ferrule 250 may simply be retained within second lumen 246 due to the confines of second lumen 246 or may be retained therein via any other suitable structures. A suture 290 is secured, or tied to ferrule 250 at the free ends 292 thereof. As best shown in FIG. 6, suture 290 is disposed about ferrule assembly 240 and extends proximally therefrom, passing through a lumen (not shown) defined within housing 210. Looped end 294 of suture 290 extends proximally from housing 210. Alternatively, suture 290 may be configured to engage ferrule 250 and extend proximally though a lumen (not shown) defined within rod 220, ultimately extending proximally from housing 210.

The operation of suturing device 200 is similar to that of suturing device 100, discussed above. First, rod 220 is fixed in position with respect to housing 210 via latch 230 according to the thickness of tissue to be sutured. As can be appreciated, rod 220 would be positioned to extend a relatively small distance from housing 210 where tissue to be sutured has a relatively small thickness and would be positioned to extend a larger distance from housing 210 where tissue to be sutured is relatively thick. Once latch 230 is closed, fixing rod 220 in position, suturing device 200 is inserted through a wound such that ferrule assembly 240 is disposed adjacent an interior face of tissue to be sutured. If adjustments are needed, tissue stop 247 is moved proximally using rod 220 and latch 230 until tissue stop 247 abuts an inner surface of tissue with tissue stop 215 in contact with an exterior surface of tissue. The latch 230 is then locked, fixing the relative positions of tissue stops 215 and 247 to define a gap therebetween.

Next, needle 270 is inserted into guide lumen 218. Guide lumen 218 directs needle 270 toward ferrule 250 upon distal translation of needle 270 therethrough. Upon further distal translation of needle 270 through tissue, distal tip 272 of needle 270 enters lumen 246 of ferrule assembly 240. Needle 270 is dimensioned such that needle 270 may translated at least partially through lumen 246 of ferrule assembly 240. Needle 270 may also define a lumen 274 therethrough, such that as needle 270 is translated through lumen 274, ferrule 250 is accepted through lumen 274 of needle 270. Ferrule 250 and lumen 274 of needle 270 are dimensioned to have a substantially similar diameter such that, as needle 270 is urged into lumen 246 of ferrule assembly 240, ferrule 250 is lodged within lumen 274 of needle 270 via a friction-fit male-female engagement.

Once ferrule 250 is lodged within needle 270, needle 270 may be translated proximally back through tissue, translating ferrule 250 through tissue as well. If suturing device 200 begins to translate proximally along with needle 270, tissue stop 247 of ferrule assembly 240 will eventually contact an interior surface of tissue to inhibit suturing device 200 from moving proximally, thereby allowing only needle 270 to move with respect to suturing device 200. Translating needle 270 and ferrule 250 further proximally and completely out of tissue leaves suture 290 disposed through tissue. More particularly, free end 292 of suture 290 are positioned on a proximal side of tissue, with suture 290 extending through tissue, exiting tissue on a distal side thereof and extending proximally through the wound in tissue to looped end 294 thereof. The positioning, or configuration of suture 290, when disposed through tissue, facilitates the tying off of suture (or sutures) 290. As such, a similar procedure as described above may be completed on an opposite side (or sides) of the wound and the sutures 290 may then be tightened and tied off to close the wound.

Figure 7:
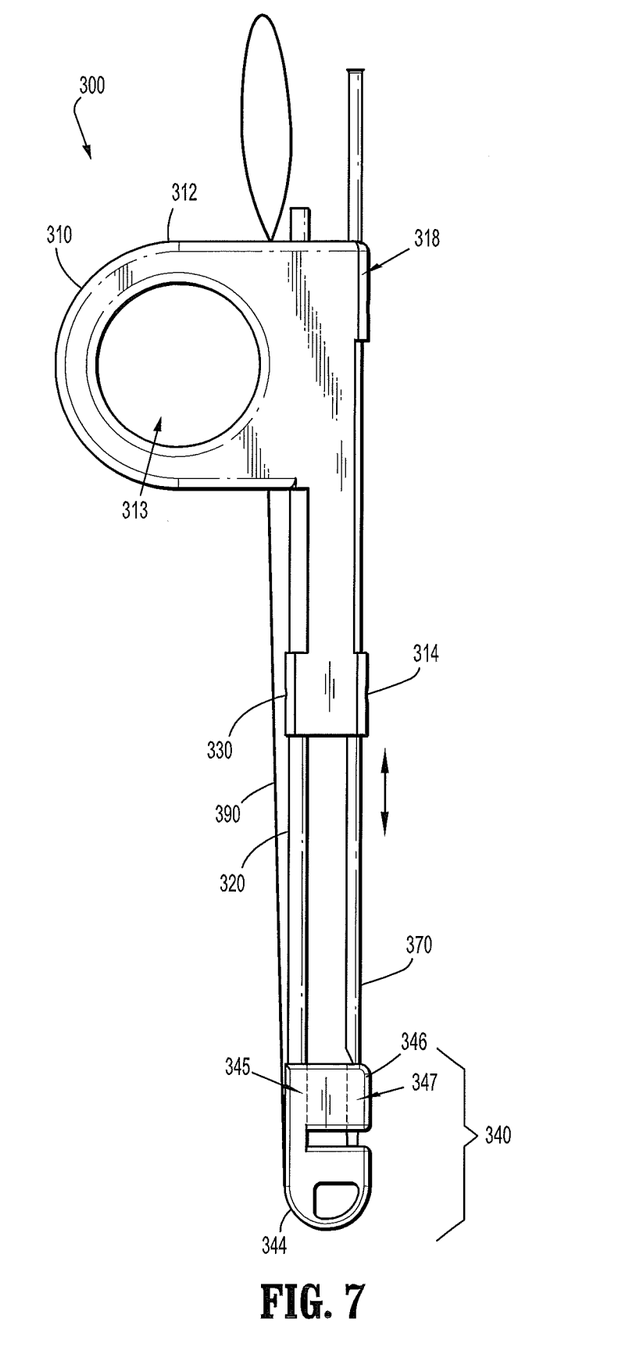
FIG. 7 is a side view of a suturing device according to yet another embodiment of the present disclosure.
Figure 8:
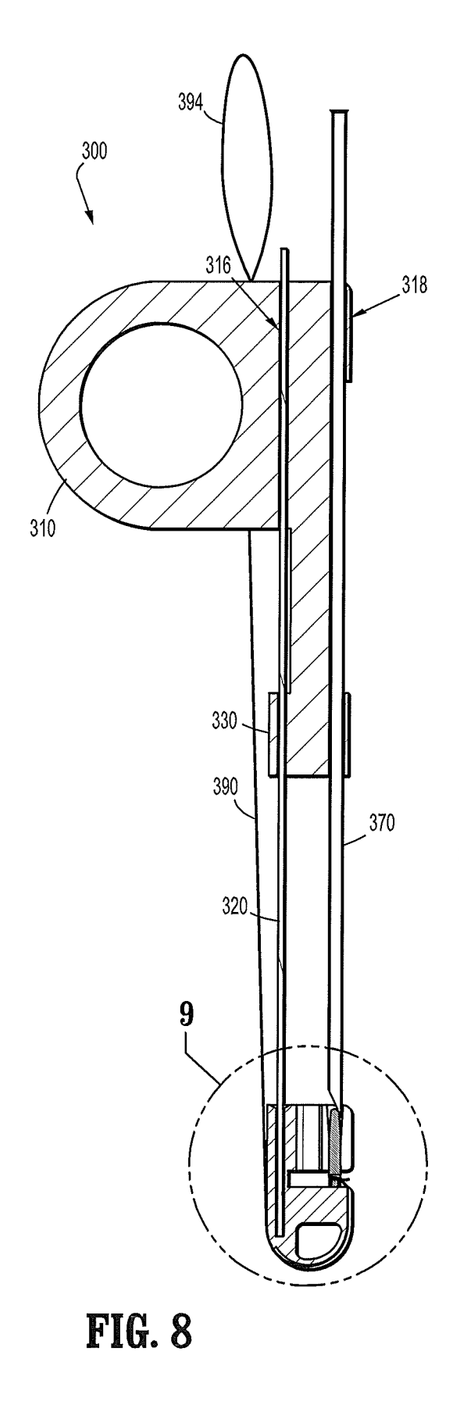
FIG. 8 is a side, cross-sectional view of the suturing device of FIG. 7.
Figure 9:
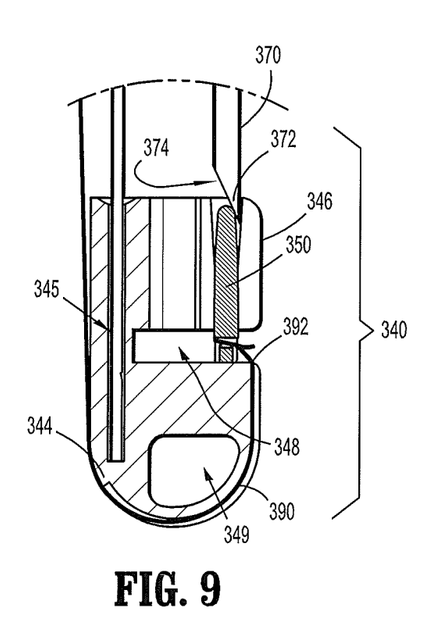
FIG. 9 is an enlarged, cross-sectional view of a ferrule assembly of the suturing device of FIG. 8.

Referring now to FIGS. 7-9, another embodiment of a suturing device 300 includes a housing 310, a ferrule assembly 340 and a needle 370. Housing 310 includes a proximal portion 312 and an elongated distal portion 314. Proximal portion 312 includes finger ring 313 defined therethrough, while distal portion 314 includes a latch 330 disposed thereon. Rod 320 is disposed through a lumen 316 defined through housing 310. Housing 310 is configured substantially similarly to housing 210 described above and thus the description thereof will not be repeated here.

With continued reference to FIGS. 7-9, ferrule assembly 340 is shown including base portion 344 and tissue stop 346. Ferrule assembly 340 further includes a first lumen 345 defined within the base portion 344 for fixedly securing rod 320 therethrough and a second lumen 347 defined within tissue stop 346 for releasably retaining ferrule 350 therein. Free end 392 of suture 390 is attached to ferrule 350, while looped end 394 of suture 390 extends around base portion 344 and proximally therefrom, ultimately extending through a lumen (not shown) defined within housing 310. Alternatively, suture 390 may be configured according to any of the embodiments above. Base portion 344 may be configured in any shape (e.g., conical) to facilitate the positioning of suturing instrument 300 through an opening in tissue. Additionally, base portion 344 may be configured to protect tissue stop 346 and ferrule 350 during insertion of suturing instrument 300 into tissue.

As best shown in FIG. 9, base portion 344 and tissue stop 346 are at least partially separated by a compliance feature 348, e.g., a slot 348 defined within ferrule assembly 340. Base portion 344 may further include an aperture 349 defined therethrough. Slot 348 and/or aperture 349 may be configured to provide some degree of compliance, or flexibility to ferrule assembly 340 to protect against damaging suturing device 300 and surrounding tissue and to facilitate the operation of suturing device, e.g., during insertion of suturing device 300 into tissue, insertion of needle 370 into ferrule assembly 340, engagement of needle 370 and ferrule 360, removal of needle 370 and ferrule 360 from ferrule assembly 340, or other similar actions wherein a force is applied to ferrule assembly 340 and/or tissue.

In operation, similar to the embodiments discussed above, needle 370 is inserted through guide lumen 318 of housing 310 and through tissue. Needle 370 is configured to translate at least partially through lumen 347 of tissue stop 346, thereby engaging ferrule 350 thereon, e.g. via a male-female friction fit engagement or a female-male friction fit engagement. Thereafter, needle 370 may be translated proximally, pulling ferrule 350 and suture 390 through tissue. The above-mentioned procedure may then be repeated as desired on opposing sides of the wound. The sutures 390 may then be tied off to close the wound.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of suturing an opening in tissue, comprising:
   inserting a suturing device through an opening in tissue, the suturing device including a housing defining a guide lumen and a ferrule assembly spaced distally from a distal end of the guide lumen to define a gap between the ferrule assembly and the distal end of the guide lumen, the ferrule assembly releasably engaging a ferrule, the ferrule retaining a portion of a suture;
   positioning the suturing device such that tissue surrounding the opening in tissue is disposed in the gap between the ferrule assembly and the distal end of the guide lumen;
   inserting a needle distally through the guide lumen defined within the housing, through tissue disposed within the gap, and at least partially into the ferrule assembly to engage the ferrule with a distal end of the needle; and
   translating the needle, with the ferrule engaged thereto, proximally through tissue disposed within the gap and the guide lumen defined within the housing to completely withdraw the ferrule and the portion of the suture from the guide lumen.

2. The method according to claim 1, further including removing the suturing device from the opening in tissue.

3. The method according to claim 2, further including repeating, on an opposite side of the opening in tissue, inserting the suturing device, positioning the suturing device, inserting the needle, translating the needle, and removing the suturing device.

4. The method according to claim 3, further including tying off the sutures to close the opening in tissue.

5. The method according to claim 1, further including adjusting the gap by repositioning the ferrule assembly with respect to the housing.

6. The method according to claim 5, wherein the gap is adjusted in accordance with a thickness of tissue to be sutured.

7. The method according to claim 5, wherein the gap is adjusted at least one of before inserting the suturing device and before inserting the needle.

* * * * *